(12) United States Patent
Abbitt et al.

(10) Patent No.: US 8,466,341 B2
(45) Date of Patent: Jun. 18, 2013

(54) MAIZE 17KD OLEOSIN SEED-PREFERRED REGULATORY ELEMENT

(75) Inventors: Shane Abbitt, Ankeny, IA (US); Jinrui Shi, Johnston, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 396 days.

(21) Appl. No.: 12/773,411

(22) Filed: May 4, 2010

(65) Prior Publication Data

US 2010/0281569 A1   Nov. 4, 2010

Related U.S. Application Data

(60) Provisional application No. 61/215,302, filed on May 4, 2009.

(51) Int. Cl.
*C12N 15/82* (2006.01)
*C07H 21/04* (2006.01)
*A01H 5/00* (2006.01)

(52) U.S. Cl.
USPC ........... 800/287; 800/278; 800/298; 800/295; 536/24.1; 435/320.1; 435/468; 435/419

(58) Field of Classification Search
None
See application file for complete search history.

(56) References Cited

U.S. PATENT DOCUMENTS

| | | | |
|---|---|---|---|
| 7,183,109 B2 * | 2/2007 | Streatfield et al. | 435/468 |
| 2007/0130645 A1 * | 6/2007 | Wu et al. | 800/278 |

OTHER PUBLICATIONS

Digeon et al. Cloning of a wheat puroindoline gene promoter by IPCR and anaylsis of promoter regions required for tissue-specific expression in transgenic rice seeds. (1999) Plant Molecular Biology; vol. 39; pp. 1101-1112.*

Genbank Accession No. U13702, Zea mays oil body protein 17 kDa oleosin (ole17) gene, complete cds, 1995, pp. 1-2.

Lee, K., et al., "Genes encoding oleosins in maize kernel of inbreds Mo17 and B73," *Plant Molecular Biology*, 1994, vol. 26, pp. 1981-1987.

* cited by examiner

*Primary Examiner* — Cathy Kingdon Worley
(74) *Attorney, Agent, or Firm* — Alston & Bird LLP

(57) ABSTRACT

The present invention provides compositions and methods for regulating expression of nucleotide sequences of interest in a plant. Compositions are novel nucleotide sequences for a seed-preferred promoter associated with the maize 17 KD OLE (17 kilodalton oleosin) coding region. A method for expressing a nucleotide sequence of interest in a plant using the regulatory sequence disclosed herein is provided.

19 Claims, 8 Drawing Sheets

```
      BamHI
      ------
  1   CGGATCCCAT GCAGGATCAG AAGCTCACAA AATAAATAGT ACTATAAATG
      GCCTAGGGTA CGTCCTAGTC TTCGAGTGTT TTATTTATCA TGATATTTAC

51   ATTAAATGGT TTATCAAATA ATTGCAGGAC TTGGGAAGTG CTTTATACAT
      TAATTTACCA AATAGTTTAT TAACGTCCTG AACCCTTCAC GAAATATGTA

103   AACACATTTT TCACCTTTTT AATGACACGA ACAGTTCTTA ACATCTTTTA
      TTGTGTAAAA AGTGGAAAAA TTACTGTGCT TGTCAAGAAT TGTAGAAAAT

HindIII
              -------
151   AAATATGTGC CTAAGCTTAC ATGTATGATC GTTAATGACC AGAATTTTGG
      TTTATACACG GATTCGAATG TACATACTAG CAATTACTGG TCTTAAAACC 201   GAAGGTCTTT GTTGTTGGTA ATTGTAATTA CAATCTTGAA TATCAGTTTG
      CTTCCAGAAA CAACAACCAT TAACATTAAT GTTAGAACTT ATAGTCAAAC EcoRI
                              -----
251   AACCATGTTT AGGCTACATT ATGTGCTATG AATTCGCGTG GAAAAATATT
      TTGGTACAAA TCCGATGTAA TACACGATAC TTAAGCGCAC CTTTTTATAA 301   GAAAAGAAAT ACAAATTACT CTCACACAA ATCTAAATAG TAAAGTAGAT
      CTTTTCTTTA TGTTTAATGA AGAGTGTGTT TAGATTTATC ATTTCATCTA 351   CTGGTTACAG AGCAGAAATT TTGAAGTGTC ATAGATAGGC TGAAAATATG
      GACCAATGTC TCGTCTTTAA AACTTCACAG TATCTATCCG ACTTTTATAC 401   TAGTCACGAG CAACACATTA CTACTTGAGG CCATCAATAC TGTTTTTTCT
      ATCAGTGCTC GTTGTGTAAT GATGAACTCC GGTAGTTATG ACAAAAAAGA 451   TCTCCAACCT ATGTAACTAT GTTATTCTTT TCCTCCTTAA ATGTAAGGCA
      AGAGGTTGGA TACATTGATA CAATAAGAAA AGGAGGAATT TACATTCCGT 501   AACCTCCTAT CCTTTTTCTT TCAAATTCAT TGCATTAACT GAGTGGTTCT
      TTGGAGGATA GGAAAAAGAA AGTTTAAGTA ACGTAATTGA CTCACCAAGA 551   TACATGTAGA AATGAAGTTG GAGCAAAGAC GCTTGGTGCG GAACCGAAAA
      ATGTACATCT TTACTTCAAC CTCGTTTCTC CGAACCACGC CTTGGCTTTT 601   TTTGTTAGTC TATAAATCAT TAGAGGGCGC CTGAAGTTCG CCAAATGTTC
      AAACAATCAG ATATTTAGTA ATCTCCCGCG GACTTCAAGC GGTTTACAAG 651   TAGTAGATTT TAGTAACCAC CCACGCTAGC TGACTCGACC ACCGTCTGCT
      ATCATCTAAA ATCATTGGTG GGTGCGATCG ACTGAGCTGG TGGCAGACGA 701   GGCTGGCGCT GTCCATGCAC ATGTACAGCC CCTGGCGCTG GCACGCACCC
      CCGACCGCGA CAGGTACGTG TACATGTCGG GGACCGCGAC CGTGCGTGGG SmaI
                                          ------
                                          AvaI
                                          ------
751   ACGGCATACC TCCCATGACT CTGACAGCCC GGGACTCCCT CCGCTCGTGC
      TGCCGTATGG AGGGTACTGA GACTGTCGGG CCCTGAGGGA GGCGAGCACG
```

FIG. 1B

```
                    AvaI
801  CGTGTCAGCC TCACTCGAGC GGTGTACTCC ATGCAAGCCT CCACCTCGGC
     GCACAGTCGG AGTGAGCTCG CCACATGAGG TACGTTCGGA GGTGGAGCCG

851  CACGTACCCC CTCCCCTTCC TTACGTGTCA CCGCTCTCGC TCCCTATATA
     GTGCATGGGG GAGGGGAAGG AATGCACAGT GGCGAGAGCG AGGGATATAT

901  CGGCTGCCTG GCCAGGCCTT TCCACTTCAC TACTCTCTCT CTCTGCCTGC
     GCCGACGGAC CGGTCCGGAA AGGTGAAGTG ATGAGAGAGA GAGACGGACG

ClaI
951  AAAGCTGCTT GATCCATCAT CGATCACATC ACTCCACCAG CCGCAGCGCT
     TTTCGACGAA CTAGGTAGTA GCTAGTGTAG TGAGGTGGTC GGCGTCGCGA

1001 CGAACGTACG ACCCATG
     GCTTGCATGC TGGGTAC
```

FIG. 1C

SEQUENCE LISTING

<160> NUMBER OF SEQ ID NOS: 1

<210> SEQ ID NO 1
<211> LENGTH: 1007
<212> TYPE: DNA
<213> ORGANISM: Zea mays

<400> SEQUENCE: 1

```
catgcaggat cagaagctca caaaataaat agtactataa atgattaaat ggtttatcaa      60
ataattgcag gacttgggaa gtgctttata cataacacat ttttcacctt tttaatgaca     120
cgaacagttc ttaacatctt ttaaaatatg tgcctaagct tacatgtatg atcgttaatg     180
accagaattt tgggaaggtc tttgttgttg gtaattgtaa ttacaatctt gaatatcagt     240
ttgaaccatg tttaggctac attatgtgct atgaattcgc gtggaaaaat attgaaaaga     300
aatacaaatt acttctcaca caaatctaaa tagtaaagta gatctggtta cagagcagaa     360
attttgaagt gtcatagata ggctgaaaat atgtagtcac gagcaacaca ttactacttg     420
aggccatcaa tactgttttt tcttctccaa cctatgtaac tatgttattc ttttcctcct     480
taaatgtaag gcaaacctcc tatcctttt ctttcaaatt cattgcatta actgagtggt      540
tcttacatgt agaaatgaag ttggagcaaa gaggcttggt gcggaaccga aaatttgtta     600
gtctataaat cattagaggg cgcctgaagt tcgccaaatg ttctagtaga ttttagtaac     660
cacccacgct agctgactcg accaccgtct gctggctggc gctgtccatg cacatgtaca     720 gccctggcg ctggcacgca cccacggcat acctcccatg actctgacag cccgggactc      780
cctccgctcg tgccgtgtca gcctcactcg agcggtgtac tccatgcaag cctccacctc     840
ggccacgtac cccctcccct tccttacgtg tcaccgctct cgctccctat atacggctgc     900
ctggccaggc ctttccactt cactactctc tctctctgcc tgcaaagctg cttgatccat     960
catcgatcac atcactccac cagccgcagc gctcgaacgt acgaccc                  1007
```

MAIZE 17KD OLEOSIN SEED-PREFERRED REGULATORY ELEMENT

CROSS-REFERENCE TO RELATED APPLICATIONS

This application claims the benefit of U.S. Provisional Patent Application No. 61/215,302, filed May 4, 2009, which is hereby incorporated herein in its entirety by reference.

FIELD OF THE INVENTION

The present invention relates to the field of plant molecular biology, more particularly to regulation of gene expression in plants.

BACKGROUND OF THE INVENTION

Expression of DNA sequences in a plant host is dependent upon the presence of operably linked regulatory elements that are functional within the plant host. Choice of the regulatory element will determine when and where within the organism the DNA sequence is expressed. Where continuous expression is desired throughout the cells of a plant, and/or throughout development, constitutive promoters are utilized. In contrast, where gene expression in response to a stimulus is desired, inducible promoters are the regulatory element of choice. Where expression in specific tissues or organs are desired, tissue-preferred promoters may be used. That is, they may drive expression in specific tissues or organs. Such tissue-preferred promoters may be temporal, constitutive, or inducible. In either case, additional regulatory sequences upstream and/or downstream from a core promoter sequence may be included in expression constructs to bring about varying levels of expression of nucleotide sequences in a transgenic plant.

As this field develops and more genes become accessible, a greater need exists for transformed plants with multiple genes. These multiple exogenous genes typically need to be controlled by separate regulatory sequences, however. Further, some genes should be regulated constitutively whereas other genes should be expressed at certain developmental stages and/or locations in the transgenic organism. Accordingly, a variety of regulatory sequences having diverse effects is needed.

Diverse regulatory sequences are also needed, as undesirable biochemical interactions can result from using the same regulatory sequence to control more than one gene. For example, transformation with multiple copies of a regulatory element may cause problems, such that expression of one or more genes may be affected.

Isolation and characterization of seed-preferred promoters and terminators that can serve as regulatory elements for expression of isolated nucleotide sequences of interest in a seed-preferred manner are needed for impacting various traits in plants and in use with scorable markers. The inventor has isolated just such a promoter.

BRIEF SUMMARY OF THE INVENTION

The present invention therefore relates to an isolated regulatory sequence that regulates transcription in a seed embryo/aleurone-preferred manner. Such regulatory sequence is preferably a sequence natively associated with, and that drives expression in, the coding regions of maize 17 KD OLE (17 Kilodalton oleosin).

The present invention further relates to recombinant expression cassettes comprising such a regulatory sequence operably linked to a nucleic acid of interest, or a vector comprising such an expression cassette.

The present invention also relates to plant cells having stably incorporated in its genome such a regulatory sequence. Such plant cells may be monocots or dicots, and could include maize, wheat, rice, barley, sorghum, millet, rye, soybeans, alfalfa, oilseed *Brassica*, cotton, sunflower, potatoes, or tomatoes. The present invention also includes plants stably transformed with such an isolated regulatory sequence, and transgenic seed obtained from such plants.

The present invention also relates to a method for modulating expression of a nucleic acid of interest in a plant, comprising introducing into a plant cell or tissue a polynucleotide molecule comprising one of the above-described regulatory sequences operably linked to a nucleic acid of interest, regenerating a plant from the plant cell wherein the plant expresses the nucleic acid of interest.

Additional detail regarding the present invention will become evident from the further description provided.

BRIEF DESCRIPTION OF THE DRAWINGS

FIGS. 1B-1C are the double stranded sequence of the ZM-17 KD OLE promoter with the features and restriction sites marked. The upper strand of the ZM-17 KD OLE promoter in FIGS. 1B-1C is set forth in SEQ ID NO: 1, and the lower strand is the complement of the sequence set forth in SEQ ID NO: 1.

DETAILED DESCRIPTION

Figure 1A:
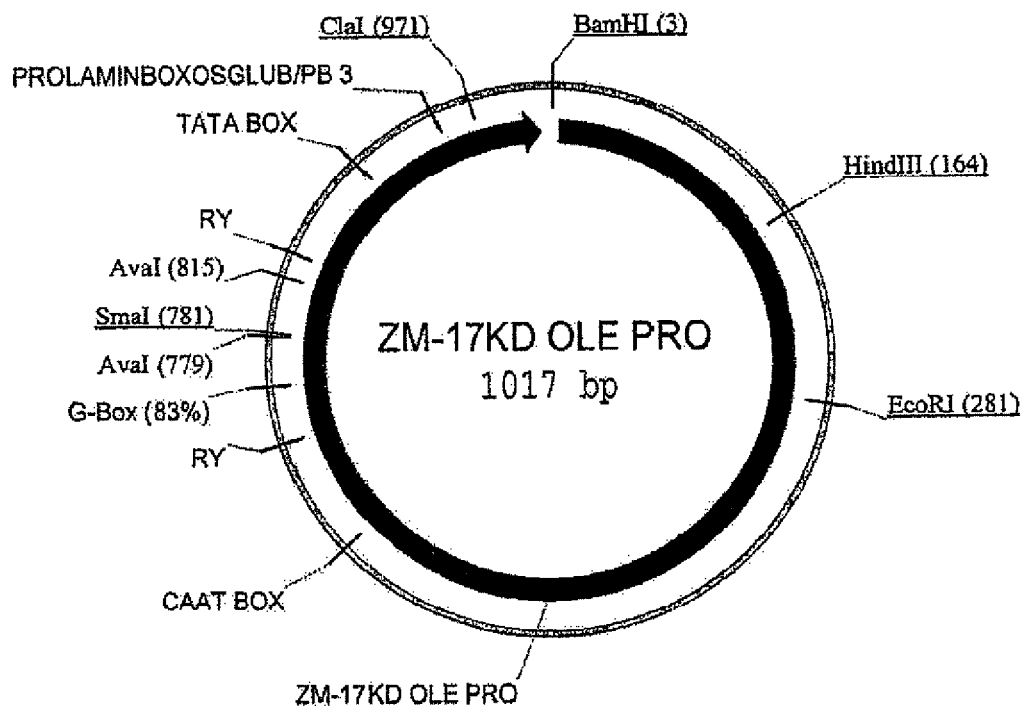
FIG. 1A shows the ZM-17 KD OLE promoter with various restriction sites and features.

The seed of monocot plants include a seed coat, the embryo, and a supply of stored food, the endosperm. Cereal endosperm mature seed includes three cell types: the aleurone cells, the starchy endosperm, and the basal endosperm transfer cells. The aleurone is a layer of densely cytoplasmic cells covering the surface of the endosperm, just beneath the maternal pericarp tissue. When the seed germinates, the aleurone cells are stimulated to secrete enzymes that break down the storage compounds in the endopersm, allowing amino acids and sugars to become available to the growing seedling, which develops from the embryo.

In accordance with the invention, nucleotide sequences are provided that allow regulation of transcription in a seed preferred manner, particularly, the embryo and/or aleurone. Thus, the compositions of the present invention comprise novel nucleotide sequences for plant regulatory elements natively associated with the nucleotide sequences coding for maize 17 kD oleosin protein, identified here as ZM-17 KD OLE.

Oleosins are 16 kD to 24 kD structural proteins on the surface of intracellular oil bodies in seeds. Oleosins in maize have been studied and three have been categorized by the molecular weight of the encoded protein: OLE16, OLE17 and OLE18. OLE16 in maize is a 16 kD oleosin, considered a low molecular weight oleosin compared to the 17 kD and 18 kD oleosins. Lee and Huang, (1994) "Genes encoding oleosins in maize kernel of inbreds Moll and B73" Plant Mol. Biol. 26(6):1981-1987.

In an embodiment, the ZM-17 KD OLE regulatory element drives transcription in a seed embryo/aleurone-preferred manner, wherein said regulatory element comprises a nucleotide sequence selected from the group consisting of: a) sequences natively associated with, and that regulate expression of DNA coding for maize 17 KD OLE (17 KD oleosin) the nucleotide sequence set forth in SEQ ID NO: 1; or c) a sequence comprising a fragment of the nucleotide sequence set forth in either of SEQ ID NO: 1.

Further embodiments are to expression cassettes, transformation vectors, plants, plant cells and plant seed comprising the above nucleotide sequences. The invention is further to methods of using the sequence in plants and plant cells. An embodiment of the invention further comprises the nucleotide sequences described above comprising a detectable marker.

During the reproduction process, angiosperms produce an ovary, which, together with its seed develop into a fruit, that is, a ripened ovary or ovaries, and adjacent parts that may be fused to it. The mature ovary wall is the seed and encloses the seeds. Manipulation of seed properties, expressing proteins to the seed, and expressing markers to the seed has numerous uses in the plant industry. A promoter expressing proteins in the seed layer is valuable for a variety of applications in expressing proteins including controlled expression in seed tissue of such proteins.

Such a promoter is also useful to target sequences encoding proteins for disease resistance to the seed. Additionally, linking a promoter which preferentially expresses to the seed with a marker, and, in particular, a visual marker, is useful in tracking the expression of a linked gene of interest.

A method for expressing an isolated nucleotide sequence in a plant using the regulatory sequences disclosed herein is provided. The method comprises transforming a plant cell with an isolated nucleotide sequence operably linked to one or more of the plant regulatory sequences of the present invention and regenerating a stably transformed plant from the transformed plant cell. In this manner, the regulatory sequences are useful for controlling the expression of endogenous as well as exogenous products in a seed-preferred manner.

Frequently it is desirable to have preferential expression of a DNA sequence in a tissue of an organism. For example, increased resistance of a plant to insect attack might be accomplished by genetic manipulation of the plant's genome to comprise a tissue-preferred promoter operably linked to an insecticide gene such that the insect-deterring substances are specifically expressed in the susceptible plant tissues. Preferential expression of the nucleotide sequence in the appropriate tissue reduces the drain on the plant's resources that occurs when a constitutive promoter initiates transcription of a nucleotide sequence throughout the cells of the plant.

Alternatively, it might be desirable to inhibit expression of a native DNA sequence within a plant's tissues to achieve a desired phenotype. In this case, such inhibition might be accomplished with transformation of the plant to comprise a tissue-preferred promoter operably linked to an antisense nucleotide sequence, such that tissue-preferred expression of the antisense sequence produces an RNA transcript that interferes with translation of the mRNA of the native DNA sequence in a subset of the plant's cells.

Under the regulation of the seed-preferred regulatory elements will be a sequence of interest, which will provide for modification of the phenotype of the seed. Such modification includes modulating the production of an endogenous product, as to amount, relative distribution, or the like, or production of an exogenous expression product to provide for a novel function or product in the seed.

Unless defined otherwise, all technical and scientific terms used herein have the same meaning as commonly understood by one of ordinary skill in the art to which this invention belongs. Unless mentioned otherwise, the techniques employed or contemplated herein are standard methodologies well known to one of ordinary skill in the art. The materials, methods and examples are illustrative only and not limiting. All references referred to are incorporated herein by reference.

Definitions

By "embryo-preferred" is intended favored spatial expression in the embryo of the seed.

By "aleurone-preferred" is intended favored spatial expression in the aleurone of the seed.

By "isolated" is intended material, such as a nucleic acid or protein, which is: (1) substantially or essentially free from components which normally accompany or interact with the material as found in its naturally occurring environment or (2) if the material is in its natural environment, the material has been altered by deliberate human intervention to a composition and/or placed at a locus in a cell other than the locus native to the material.

By "nucleic acids providing improved output traits" is intended genes that confer or contribute to an altered plant characteristic.

By "nucleic acids providing improved agronomic traits" is intended genes that confer or contribute to one or more agronomic traits.

By "ovary" is meant the ripened ovary or ovaries, and adjacent parts that may be fused to it.

By "promoter" is intended a regulatory region of DNA capable of regulating the transcription of a sequence linked thereto. It usually comprises a TATA box capable of directing RNA polymerase II to initiate RNA synthesis at the appropriate transcription initiation site for a particular coding sequence.

By "regulatory element" is intended sequences responsible for the expression of the associated transcript including, but not limited to, promoters, terminators, enhancers, introns, and the like.

By "regulatory sequence" is intended the nucleotide sequence comprising the nucleotide sequence of a regulatory element including, but not limited to, promoters, terminators, enhancers, introns, and the like. A "regulatory sequence" can comprise the nucleotide sequence of one regulatory element, or two or more regulatory elements such as, for example, a regulatory sequence comprising the combined nucleotide sequences of a promoter and an enhancer.

By "seed-preferred" is intended favored expression in the seed, the wall of the ovary of a plant, and the like including but not limited to the aleurone and embryo.

By "terminator" is intended sequences that are needed for termination of transcription: a regulatory region of DNA that causes RNA polymerase to disassociate from DNA, causing termination of transcription.

A promoter may additionally comprise other recognition sequences generally positioned upstream or 5' to the TATA box, referred to as upstream promoter elements, which influence the transcription initiation rate and further include elements which impact spatial and temporal expression of the linked nucleotide sequence. It is recognized that having identified the nucleotide sequences for the promoter region disclosed herein, it is within the state of the art to isolate and identify further regulatory elements in the 5' region upstream from the particular promoter region identified herein. Thus the promoter region disclosed herein may comprise upstream regulatory elements such as those responsible for tissue and temporal expression of the coding sequence, and may include enhancers, the DNA response element for a transcriptional regulatory protein, ribosomoal binding sites, transcriptional start and stop sequences, translational start and stop sequences, activator sequences and the like.

In the same manner, the promoter elements which enable expression in the desired tissue such as the seed can be identified, isolated, and used with other core promoters to confirm seed-preferred expression. By core promoter is meant the minimal sequence required to initiate transcription, such as the sequence called the TATA box which is common to promoters in genes encoding proteins. Thus the upstream region of ZM 17 KD-OLE can optionally be used in conjunction with its own or core promoters from other sources. The promoter may be native or non-native to the cell in which it is found.

The isolated promoter sequence of the present invention can be modified to provide for a range of expression levels of the isolated nucleotide sequence. Less than the entire promoter region can be utilized and the ability to drive seed-preferred expression retained.

It is recognized that expression levels of mRNA can be modulated with specific deletions of portions of the promoter sequence. Thus, the promoter can be modified to be a weak or strong promoter. Generally, by "weak promoter" is intended a promoter that drives expression of a coding sequence at a low level. By "low level" is intended levels of about 1/10,000 transcripts to about 1/100,000 transcripts to about 1/500,000 transcripts. Conversely, a strong promoter drives expression of a coding sequence at a high level, or at about 1/10 transcripts to about 1/100 transcripts to about 1/1,000 transcripts. Generally, at least about 20 nucleotides of an isolated promoter sequence will be used to drive expression of a nucleotide sequence.

It is recognized that to increase transcription levels enhancers can be utilized in combination with the promoter regions of the invention. Enhancers are nucleotide sequences that act to increase the expression of a promoter region. Enhancers are known in the art and include the SV40 enhancer region, the 35S enhancer element, and the like.

The promoter of the present invention can be isolated from the 5' region of its native coding region or 5' untranslated region (5' UTR). Likewise the terminator can be isolated from the 3' region flanking its respective stop codon. Methods for isolation of promoter regions are well known in the art.

Figure 2A:
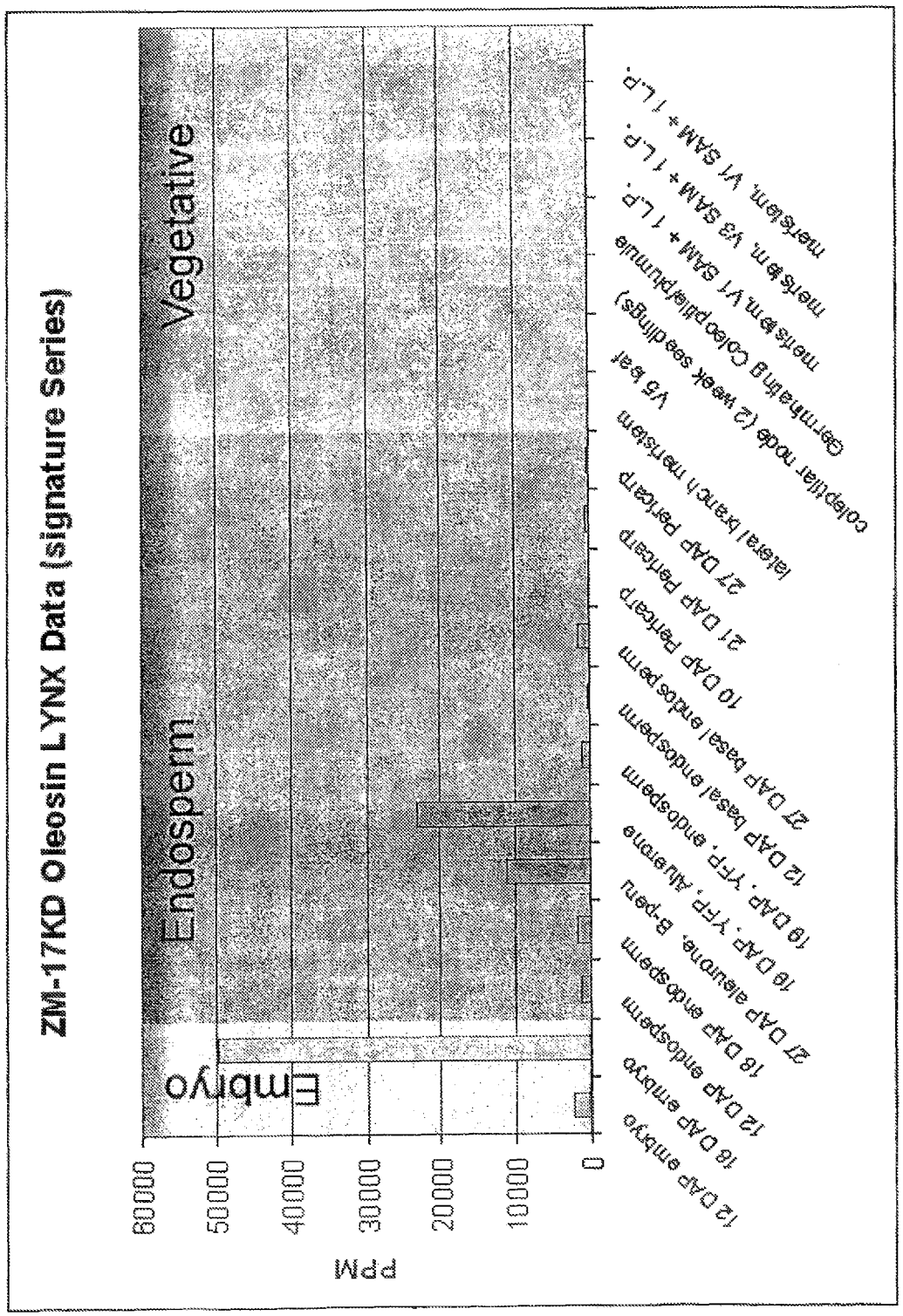
FIG. 2A shows the summary of LYNX™ data illustrating the native expression of ZM-17 KD Oleosin in *zea mays*.
Figure 3A:
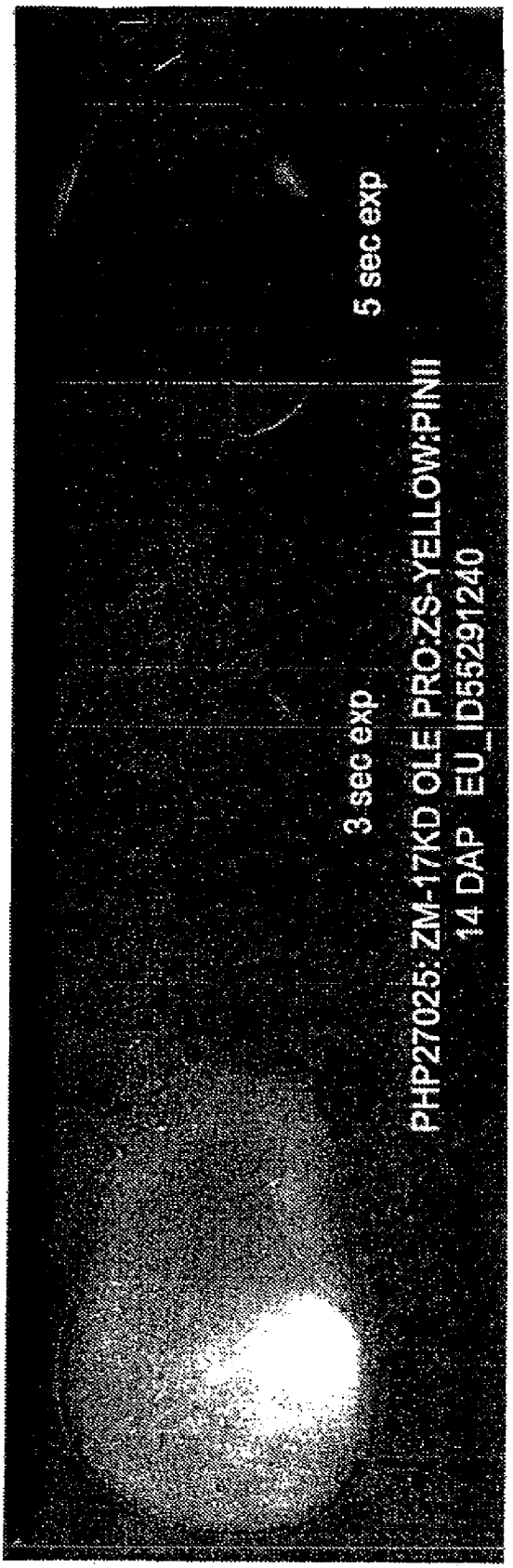
FIGS. 3A-3D are photographs taken at 14 (3A), 16 (3B), 22 (3C), and 27 (3D) days after pollination of seeds from plants with the ZS-YELLOW ZM-17 KD OLE construct. As can be seen the results demonstrate preferred expression of the ZS-YELLOW marker in the embryo and aleurone.
Figure 3B:
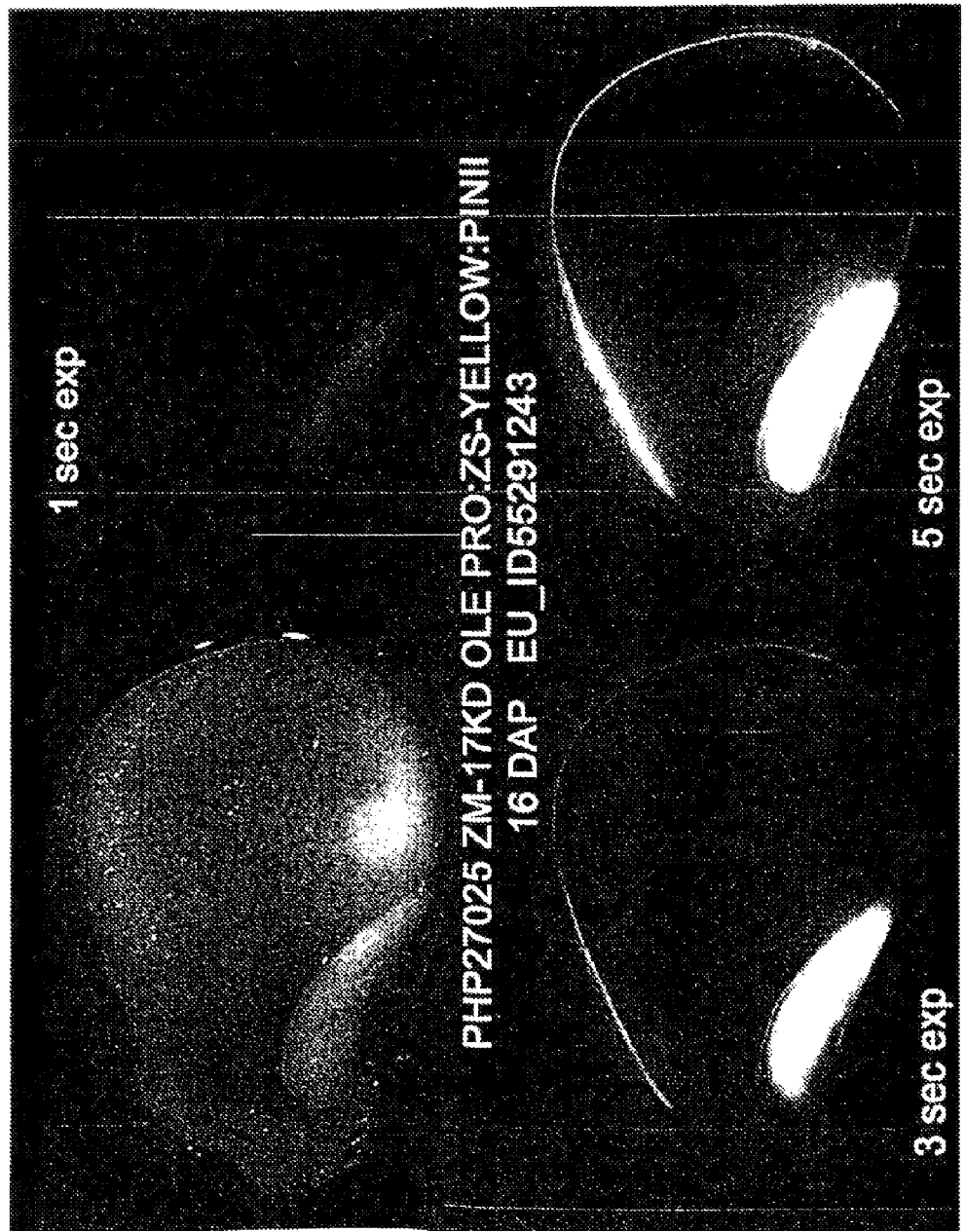
Figure 3C:
Figure 3D:
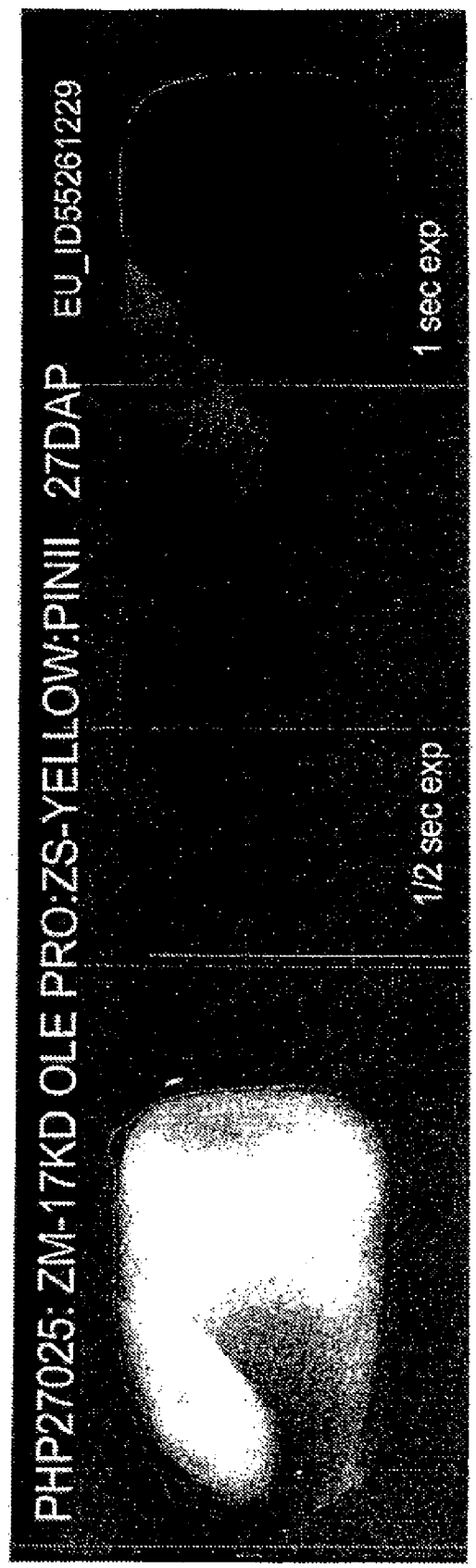

The ZM-17 KD OLE promoter set forth in SEQ ID NO:1 is 1007 nucleotides in length and is set forth in FIG. 1 (SEQ ID NO: 1). The ZM-17 KD-OLE promoter was isolated from the Zea mays ZM-17 KD-OLE coding region. It was isolated based on MPSS (Massively Parallel Signature Sequencing) technology from LYNX™ (see Brenner et al, Nature Biotechnology 18:630-634 (2000)) expression analysis showing strong expression in 18 days after expression in the embryo and 19-27 days after pollination in the aleurone. pollination) maize seed. The results of the native expression analysis can be found in FIG. 2A.

Motifs of about six or eight bases within the ZM-17 KD-OLE promoter sequence were discovered by searching for sequences of similar size and within 100 bases of the position in which they were located in various homologous maize promoters based upon the reference K. Higo, Y. Ugawa, M. Iwamoto and T. Korenaga (1999) Plant cis-acting regulatory DNA elements (PLACE) database:1999. Nucleic Acids Research Vol.27 No.1 pp. 297-300. The following motifs were identified as represented in Table 1. See also Figures 1A and 1B.

TABLE 1

| Motif Sequence | TACGTGTC | ACGTGKC | ACGTG | ACGT | ACGTGTC |
|---|---|---|---|---|---|
| Motif Length | 8 | 7 | 5 | 4 | 7 |
| Motif Core | NA | NA | NA | NA | NA |
| Motif Name | ACGTABREMOTIFAOSOSEM | ACGTABREMOTIFA2OSEM | ABRELATERD1 | ACGTATERD1 | GADOWNAT |
| Motif Description | ABRE motif A found in the promoter of the rice (O.s.) Osem ABRE; ACGT-containing ABRE; Required for ABA-responsiveness and VP1 activation; Binding site of TRAB1; Motif A and CE3 (S000282) are functionally equivalent; TRAB1, bZIP transcription factor, interacts with VP1 and mediates abscisic acid-induced transcription; | Experimentally determined sequence requirement of ACGT-core of motif A in ABRE of the rice gene, OSEM; See S000281; DRE and ABRE are independent in the ABA-responsive expression of the rd29A in Arabidopsis; K = G/T; | ABRE-like sequence from -199 to -195) required for etiolation-induced expression of erd1 (early responsive to dehydration) in Arabidopsis; | ACGT sequence (from -155 to -152) required for etiolation-induced expression of erd1 (early responsive to dehydration) in Arabidopsis; | Sequence present in 24 genes in the GA-down regulated d1 cluster (106 genes) found in Arabidopsis seed germination; This motif is similar to ABRE (Busk and Pages 1998); |
| Source Species | x | x | x | x | x |
| Monocot or Dicot | x | x | x | x | x |
| Nuclear or Chloroplast | x | x | x | x | x |

TABLE 1-continued

| | | | | | |
|---|---|---|---|---|---|
| Core or Regulon | x | x | x | x | x |
| Expression Summary | x | x | x | x | x |
| Transcription Factor Family | x | x | x | x | x |
| Transcription Factor | x | x | x | x | x |
| Transcription Factor Synonyms | x | x | x | x | x |
| Primary Reference | Unknown | Unknown | Unknown | Unknown | Unknown |
| Experimental or Computational | x | x | x | x | x |
| Motif Sequence | CATGCAC | ACGT | GTAC | TGTCA | YACT |
| Motif Length | 6 | 4 | 4 | 5 | 4 |
| Motif Core | NA | NA | NA | NA | NA |
| Motif Name | RYREPEATBNNAPA | ACGTATERD1 | CURECORECR | BIHD1OS | CACTFTPPCA1 |
| Motif Desctiption | RY repeat" "found in RY/G box (the complex containing the two Ry repeats and the G-box) of napA gene in *Brassica nampu* (B.n.); Found between −78 and −50; Required for seed specific expression; See S000262, S000263; dist B ABRE mediated transactivation by ABI3 and ABI3-dependent response to ABA; a tetramer of the composite RY/G complex mediated only ABA-independent transactivation by ABI3; B2 domain of ABI3 is necessary for ABA-independent and ABA-dependent activation through the dist B ABRE;" | ACGT sequence (from −155 to −152) required for etiolation-induced expression of erd1 (early responsive to dehydration in *Arabidopsis*; | GTAC is the core of a CuRE (copper-response element) found in Cyc6 and Cpx1 genes in *Chlamydomonas*; Also involved in oxygen-response of these genes; For CuRE, see Quin and Merchant, 1995; | Binding site of OsBIHD1, a rice BELL homeodomain transcription factor; | Tetranucleotide (CACT) is a key component of Mem1 (mesophyll expression module 1) found in the cis-regulatory element of the phosphoenolpyruvate carboxylase (ppcA1) of the C4 dicot *F. trinervia*; Y = T/C; |
| Source Species | x | x | *Chlamydomonas* | *Oryza sativa* | x |
| Monocot or Dicot | x | x | *Chlamydomonas* | monocot | x |
| Nuclear or Chloroplast | x | x | *Chlamydomonas* | nuclear | x |
| Core or Regulon | x | x | Regulon | Regulon | x |
| Expression Summary | x | x | x | x | x |
| Transcription Factor Family | x | x | x | x | x |
| Transcription Factor | x | x | x | x | x |
| Transcription Factor Synonyms | x | x | x | x | x |

TABLE 1-continued

| | | | | | |
|---|---|---|---|---|---|
| Primary Reference | Unknown | Unknown | Unknown | Unknown | Unknown |
| Experimental or Computational | x | x | x | x | x |
| Motif Sequence | AAAATATCT | CACGCAAT | | | |
| Motif Length | 9 | 8 | | | |
| Motif Core | | NA | | | |
| Motif Name | EVENINGAT | CACGCAAT | | | |
| Motif Description | Evening element found 46 times in the promoters of 31 cycling genes in *Arabidopsis thaliana* (Harmer et al. 2000); Required for circadian control of gene expression; "EE (evening element) motif"; Also found in the promoter of the *Solanum melongena* gene encoding cysteine protease, and identified as cis-element for its circadian regulation (Rawat et al. 2005); | Sequence found in D4 element in Soybean (G.m.) GH3 gene promoter; Showed constitutive activity with TGTCTC element (See S000270); Confers auxin inducibility; Binding site of nuclear protein; See also S000369; | | | |
| Source Species | | x | | | |
| Monocot or Dicot | | x | | | |
| Nuclear or Chloroplast | | x | | | |
| Core or Regulon | | x | | | |
| Expression Summary | | x | | | |
| Transcription Factor Family | | x | | | |
| Transcription Factor | x | x | | | |
| Transcription Factor Synonyms | x | | | | |
| Primary Reference | Unknown | Unknown | | | |
| Experimental or Computational | x | x | | | |

Compositions of the invention include promoters that are involved in driving the expression of an operably linked nucleic acid of interest in a seed-preferred manner. In particular, the present invention provides for isolated polynucleotide comprising the nucleotide sequence shown in SEQ ID NO: 1, and fragments and variants thereof that are capable of regulating the expression of operably linked nucleic acid of interest in a seed-preferred manner.

The invention encompasses isolated or substantially purified polynucleotide compositions. An "isolated" or "purified" polynucleotide, or biologically active portion thereof, is substantially or essentially free from components that normally accompany or interact with the polynucleotide as found in its naturally occurring environment. Thus, an isolated or purified polynucleotide is substantially free of other cellular material, or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived.

Fragments and variants of the disclosed polynucleotides are also encompassed by the present invention. By "fragment" is intended a portion of the polynucleotide portion of the amino acid sequence and hence protein encoded thereby. Fragments of a polynucleotide may retain biological activity and hence promoter activity, particularly seed-preferred promoter activity. Alternatively, fragments of a polynucleotide that are useful as hybridization probes generally do not retain biological activity. Thus, fragments of a nucleotide sequence may range from at least about 20 nucleotides, about 50 nucleotides, about 100 nucleotides, and up to the full-length polynucleotide of the invention.

A fragment of a promoter polynucleotide of the invention may encode a biologically active portion of a seed-preferred promoter, or it may be a fragment that can be used as a hybridization probe or PCR primer using methods disclosed below. A biologically active portion of a promoter of the invention can be prepared by isolating a portion of one of the promoter polynucleotides of the invention and assessing the promoter activity of the portion of the promoter in a plant or cell transformed therewith. Polynucleotides that are fragments of seed-preferred promoter nucleotide sequence comprise at least 16, 20, 50, 75, 100, 150, 200, 250, 300, 350, 400, 450, 500, 550, 600, 650, 700, 800, 900, or 1,000 contiguous nucleotides, or up to the number of nucleotides present in a full-length promoter polynucleotide disclosed herein (for example, 1007 nucleotides for SEQ ID NO: 1).

"Variants" is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotide, such as those generated, for example, by using site-directed mutagenesis. Generally, variants of a particular polynucleotide of the invention will have at least about 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

The polynucleotides of the invention include both the naturally occurring sequences as well as mutant forms. Such variants will continue to possess the desired seed-perferred promoter activity.

Variant polynucleotides also encompass sequences derived from a mutagenic and recombinogenic procedure such as DNA shuffling. With such a procedure, one or more different promoter sequences can manipulated to create a new promoter sequence possessing the desired properties. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art.

See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The polynucleotides of the invention can be used to isolate corresponding sequences from other organisms, particularly other plants, more particularly other monocots. In this manner, methods such as PCR, hybridization, and the like can be used to identify such sequences based on their sequence homology to the sequence set forth herein. Sequences isolated based on their sequence identity to the entire promoter sequence set forth herein or to variants and fragments thereof are encompassed by the present invention. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences share at least 75%, 80%, 85%, 90%, 91%, 92%, 93%, 94%, 95%, 96%, 97%, 98%, 99%, or greater sequence identity. Functions of orthologs are often highly conserved among species. Thus, isolated polynucleotides that have promoter activity and which hybridize under stringent conditions to the promoter sequence disclosed herein, or to variants or fragments thereof, are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}$P, or any other detectable marker. Thus, for example, probes for hybridization can be made by labeling synthetic oligonucleotides based on the promoter polynucleotides of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, an entire promoter polynucleotide disclosed herein, or one or more portions thereof, may be used as a probe capable of specifically hybridizing to corresponding promoter polynucleotide. To achieve specific hybridization under a variety of conditions, such probes include sequences that are unique among the polynucleotide sequences and are optimally at least about 10 nucleotides in length, and most optimally at least about 20 nucleotides in length. Such probes may be used to amplify a corresponding promoter polynucleotide from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

The following terms are used to describe the sequence relationships between two or more polynucleotides or polypeptides: (a) "reference sequence", (b) "comparison window", (c) "sequence identity", and, (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et at (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See www.ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The use of the term "polynucleotide" is not intended to limit the present invention to polynucleotides comprising DNA. Those of ordinary skill in the art will recognize that polynucleotides, can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures, and the like.

The promoter regions of the invention may be isolated from any plant, including, but not limited to corn (*Zea mays*), oilseed *Brassica* (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum*), millet (*Panicum* spp.), potato (*Solanum tuberosum*), peanuts (*Arachis hypogaea*), cotton (*Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), oats (*Avena sativa*), barley (*Hordeum vulgare*), vegetables, ornamentals, and conifers. Preferably, plants include corn, soybean, sunflower, safflower, oilseed *Brassica*, wheat, millet, barley, rye, rice, alfalfa, and sorghum.

Promoter sequences from other plants may be isolated according to well-known techniques based on their sequence homology to the homologous coding region of the coding sequences set forth herein. In these techniques, all or part of the known coding sequence is used as a probe which selectively hybridizes to other sequences present in a population of cloned genomic DNA fragments (i.e. genomic libraries) from a chosen organism. Methods are readily available in the art for the hybridization of nucleic acid sequences. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York (1993); and *Current Protocols in Molecular Biology*, Chapter 2, Ausubel, et al., eds., Greene Publishing and Wiley-Interscience, New York (1995).

"Functional variants" of the regulatory sequences are also encompassed by the compositions of the present invention. Functional variants include, for example, the native regulatory sequences of the invention having one or more nucleotide substitutions, deletions or insertions. Functional variants of the invention may be created by site-directed mutagenesis, induced mutation, or may occur as allelic variants (polymorphisms).

As used herein, a "functional fragment" is a regulatory sequence variant formed by one or more deletions from a larger regulatory element. For example, the 5' portion of a promoter up to the TATA box near the transcription start site can be deleted without abolishing promoter activity, as described by Opsahl-Sorteberg, H-G. et al., "Identification of a 49-bp fragment of the HvRLTP2 promoter directing aleruone cell specific expression" *Gene* 341:49-58 (2004). Such variants should retain promoter activity, particularly the ability to drive expression in seed or seed tissues. Activity can be measured by Northern blot analysis, reporter activity measurements when using transcriptional fusions, and the like. See, e.g., Sambrook et al. (1989) *Molecular Cloning: A Laboratory Manual* (2nd ed. Cold Spring Harbor Laboratory, Cold Spring Harbor, N.Y.), herein incorporated by reference.

Functional fragments can be obtained by use of restriction enzymes to cleave the naturally occurring regulatory element nucleotide sequences disclosed herein; by synthesizing a nucleotide sequence from the naturally occurring DNA sequence; or can be obtained through the use of PCR technology. See Mullis et al. (1987) *Methods Enzymol.* 155:335-350; Erlich, ed. (1989) *PCR Technology* (Stockton Press, New York).

For example, a routine way to remove part of a DNA sequence is to use an exonuclease in combination with DNA amplification to produce unidirectional nested deletions of double stranded DNA clones. A commercial kit for this purpose is sold under the trade name Exo-Size™ (New England Biolabs, Beverly, Mass.). Briefly, this procedure entails incubating exonuclease III with DNA to progressively remove nucleotides in the 3' to 5' direction at 5' overhangs, blunt ends or nicks in the DNA template. However, exonuclease III is unable to remove nucleotides at 3', 4-base overhangs. Timed digests of a clone with this enzyme produces unidirectional nested deletions.

The entire promoter sequence or portions thereof can be used as a probe capable of specifically hybridizing to corresponding promoter sequences. To achieve specific hybridization under a variety of conditions, such probes include sequences that are unique and are preferably at least about 10 nucleotides in length, and most preferably at least about 20 nucleotides in length. Such probes can be used to amplify corresponding promoter sequences from a chosen organism by the well-known process of polymerase chain reaction (PCR). This technique can be used to isolate additional promoter sequences from a desired organism or as a diagnostic assay to determine the presence of the promoter sequence in an organism. Examples include hybridization screening of plated DNA libraries (either plaques or colonies. See, e.g., Innis et al. (1990) *PCR Protocols, A Guide to Methods and Applications*, eds., Academic Press).

The seed-preferred regulatory elements disclosed in the present invention, as well as variants and fragments thereof, are useful in the genetic manipulation of any plant when operably linked with an isolated nucleotide sequence of interest whose expression is to be controlled to achieve a desired phenotypic response.

By "operably linked" is intended a functional linkage between a promoter and a second sequence, wherein the promoter sequence initiates and mediates transcription of the DNA sequence corresponding to the second sequence. The expression cassette will include 5' and 3' regulatory sequences operably linked to at least one of the sequences of the invention.

In one typical embodiment, in the context of an expression cassette, operably linked means that the nucleotide sequences being linked are contiguous and, where necessary to join two or more protein coding regions, contiguous and in the same reading frame. In the case where an expression cassette contains two or more protein coding regions joined in a contiguous manner in the same reading frame, the encoded polypeptide is herein defined as a "heterologous polypeptide" or a "chimeric polypeptide" or a "fusion polypeptide". The cassette may additionally contain at least one additional coding sequence to be co-transformed into the organism. Alternatively, the additional coding sequence(s) can be provided on multiple expression cassettes.

The regulatory elements of the invention can be operably linked to the isolated nucleotide sequence of interest in any of several ways known to one of skill in the art. The isolated nucleotide sequence of interest can be inserted into a site within the genome which is 3' to the promoter of the invention using site specific integration as described in U.S. Pat. No. 6,187,994, incorporated by reference herein in its entirety.

The regulatory elements of the invention can be operably linked in expression cassettes along with isolated nucleotide sequences of interest for expression in the desired plant, more particularly in the seed of the plant. Such an expression cassette is provided with a plurality of restriction sites for insertion of the nucleotide sequence of interest under the transcriptional control of the regulatory elements.

The isolated nucleotides of interest expressed by the regulatory elements of the invention can be used for directing expression of a sequence in the seed or plant. This can be achieved by increasing expression of endogenous or exogenous products in seed. Alternatively, the results can be achieved by providing for a reduction of expression of one or more endogenous products, particularly enzymes or cofactors in the seed. This down regulation can be achieved through many different approaches known to one skilled in the art, including antisense, cosupression, use of hairpin formations, or others, and discussed infra. Importation or exportation of a cofactor also allows for control of seed composition. It is recognized that the regulatory elements may be used with their native or other coding sequences to increase or decrease expression of an operably linked sequence in the transformed plant or seed.

General categories of genes of interest for the purposes of the present invention include for example, those genes involved in information, such as zinc fingers; those involved in communication, such as kinases; and those involved in housekeeping, such as heat shock proteins. More specific categories of transgenes include genes encoding important traits for agronomics, insect resistance, disease resistance, herbicide resistance, and grain characteristics. Still other categories of transgenes include genes for inducing expression of exogenous products such as enzymes, cofactors, and hormones from plants and other eukaryotes as well as prokaryotic organisms.

Modifications that affect grain traits include increasing the content of oleic acid, or altering levels of saturated and unsaturated fatty acids. Likewise, the level of seed proteins, particularly modified seed proteins that improve the nutrient value of the seed, can be increased. This is achieved by the expression of such proteins having enhanced amino acid content.

Increasing the levels of lysine and sulfur-containing amino acids may be desired as well as the modification of starch type and content in the seed. Hordothionin protein modifications are described in WO 94/16078, filed Apr. 10, 1997; WO 96/38562, filed Mar. 26, 1997; WO 96/38563, filed Mar. 26, 1997; and U.S. Pat. No. 5,703,409, issued Dec. 30, 1997. Another example is lysine and/or sulfur-rich seed protein encoded by the soybean 2S albumin described in WO 97/35023, filed Mar. 20, 1996, and the chymotrypsin inhibitor from barley, Williamson et al. (1987) *Eur. J. Biochem.* 165: 99-106.

Agronomic traits in seeds can be improved by altering expression of genes that: affect the response of seed or seed growth and development during environmental stress, Cheikh-N et al. (1994) *Plant Physiol.* 106(1):45-51) and genes controlling carbohydrate metabolism to reduce kernel abortion in maize, Zinselmeier et al. (1995) *Plant Physiol.* 107(2):385-391.

Modulation of nucleic acid expression (upregulating, downregulating, localizing, etc.) is therefore useful in many respects in plants. It is recognized that any nucleic acid of interest, including the native coding sequence, can be operably linked to the regulatory elements of the invention and expressed in the seed.

By way of illustration, without intending to be limiting, are examples of the types of genes which can be used in connection with the regulatory sequences of the invention.

1. Transgenes that provide improved output traits, including the following non-limiting examples:
  (A) Altered fatty acids, for example, by
    (1) Down-regulation of stearoyl-ACP desaturase to increase stearic acid content of the plant. See Knultzon et al., *Proc. Natl. Acad. Sci. USA* 89: 2624 (1992) and WO99/64579 (Genes for Desaturases to Alter Lipid Profiles in Corn);
    (2) Elevating oleic acid via FAD-2 gene modification and/or decreasing linolenic acid via FAD-3 gene modification. See U.S. Pat. Nos. 6,063,947; 6,323,392; 6,372,965 and WO 93/11245);
    (3) Altering conjugated linolenic or linoleic acid content, such as in WO 01/12800;
    (4) Altering LEC1, AGP, Dek1, Superal1, milps, various lpa genes such as lpa1, lpa3, hpt or hggt. For example, see WO 02/42424, WO 98/22604, WO 03/011015, U.S. Pat. No. 6,423,886, U.S. Pat. No. 6,197,561, U.S. Pat. No. 6,825,397, US2003/0079247, US2003/0204870, WO02/057439, WO03/011015 and Rivera-Madrid, R. et. al. *Proc. Natl. Acad. Sci.* 92:5620-5624 (1995).
  (B) Altered phosphorus content, for example, by the
    (1) Introduction of a phytase-encoding gene would enhance breakdown of phytate, adding more free phosphate to the transformed plant. See, e.g., Van Hartingsveldt et al., *Gene* 127: 87 (1993), for a disclosure of the nucleotide sequence of an *Aspergillus niger* phytase gene.
    (2) Up-regulation of a gene that reduces phytate content. In maize, this, for example, could be accomplished, by cloning and then re-introducing DNA associated with one or more of the alleles, such as the LPA alleles, identified in maize mutants characterized by low levels of phytic acid, such as in Raboy et al., *Maydica* 35: 383 (1990) and/or by altering inositol kinase activity as in WO 02/059324, US2003/0009011, WO 03/027243, US2003/0079247, WO 99/05298, U.S. Pat. Nos. 6,197,561, 6,291,224, 6,391,348, WO2002/059324, US2003/0079247, WO98/45448, WO99/55882, WO01/04147.
  (C) Altered carbohydrates effected, for example, by altering a gene for an enzyme that affects the branching pattern of starch or a gene altering thioredoxin. See U.S. Pat. No. 6,531,648; see also Shiroza et al., J. Bacteriol. 170: 810 (1988) (nucleotide sequence of *Streptococcus mutans* fructosyltransferase gene); Steinmetz et al., Mol. Gen. Genet. 200: 220 (1985) (nucleotide sequence of *Bacillus subtilis* levansucrase gene); Pen et al., Bio/Technology 10: 292 (1992) (production of transgenic plants that express *Bacillus licheniformis* alpha-amylase); Elliot et al., Plant Molec. Biol. 21: 515 (1993) (nucleotide sequences of tomato invertase genes); Sogaard et al., J. Biol. Chem. 268: 22480 (1993) (site-directed mutagenesis of barley alpha-amylase gene); Fisher et al., Plant Physiol. 102: 1045 (1993) (maize endosperm starch branching enzyme II); WO 99/10498 (improved digestibility and/or starch extraction through modification of UDP-D-xylose 4-epimerase, Fragile 1 and 2, Ref1, HCHL, C4H); U.S. Pat. No. 6,232,529 (method of producing high oil seed by modification of starch levels (AGP)). The fatty acid modification genes mentioned above may also be used to affect starch content and/or composition through the interrelationship of the starch and oil pathways.
  (D) Altered antioxidant content or composition, such as alteration of tocopherol or tocotrienols. See, e.g., U.S. Pat. No. 6,787,683, US2004/0034886 and WO 00/68393 involving the manipulation of antioxidant levels through alteration of a phytl prenyl transferase (ppt), WO 03/082899 through alteration of a homogentisate geranyl geranyl transferase (hggt).

(E) Altered essential seed amino acids. See, e.g., U.S. Pat. No. 6,127,600 (method of increasing accumulation of essential amino acids in seeds); U.S. Pat. No. 6,080,913 (binary methods of increasing accumulation of essential amino acids in seeds); U.S. Pat. No. 5,990,389 (high lysine); U.S. Pat. No. 5,850,016 (alteration of amino acid compositions in seeds); WO98/20133 (proteins with enhanced levels of essential amino acids); U.S. Pat. No. 5,885,802 (high methionine); U.S. Pat. No. 5,885,801 (high threonine); U.S. Pat. No. 6,664,445 (plant amino acid biosynthetic enzymes), U.S. Pat. No. 6,459,019 (increased lysine and threonine); U.S. Pat. No. 6,441,274 (plant tryptophan synthase beta subunit); U.S. Pat. No. 6,346,403 (methionine metabolic enzymes); U.S. Pat. No. 5,939,599 (high sulfur); U.S. Pat. No. 5,912,414 (increased methionine); U.S. Pat. No. 5,633,436 (increasing sulfur amino acid content); U.S. Pat. No. 5,559,223 (synthetic storage proteins with defined structure containing programmable levels of essential amino acids for improvement of the nutritional value of plants); U.S. Pat. No. 6,194,638 (hemicellulose); U.S. Pat. No. 6,194,638 (RGP); U.S. Pat. No. 6,399,859 and US2004/0025203 (UDPGdH); US2003/0163838, US2003/0150014, US2004/0068767, U.S. Pat. No. 6,803,498, WO01/79516, and WO00/09706 (CesA: cellulose synthase); WO98/56935 (plant amino acid biosynthetic enzymes); WO98/45458 (engineered seed protein having higher percentage of essential amino acids); WO98/42831 (increased lysine); WO96/01905 (increased threonine); WO95/15392 (increased lysine); WO99/40209 (alteration of amino acid compositions in seeds); WO99/29882 (methods for altering amino acid content of proteins).

2. Transgenes that provide improved agronomic traits such as the following non-limiting examples:

Genes that affect abiotic stress resistance (including but not limited to flowering, ear and seed development, enhancement of nitrogen utilization efficiency, altered nitrogen responsiveness, drought resistance or tolerance, cold resistance or tolerance, and salt resistance or tolerance) and increased yield under stress. See, e.g., WO 00/73475 (water use efficiency is altered through alteration of malate); U.S. Pat. Nos. 5,892,009, 5,965,705, 5,929,305, 5,891,859, 6,417,428, 6,664,446, 6,706,866, 6,717,034, 6,801,104, WO2000/060089, WO2001/026459, WO2001/035725, WO2001/034726, WO2001/035727, WO2001/036444, WO2001/036597, WO2001/036598, WO2002/015675, WO2002/017430, WO2002/077185, WO2002/079403, WO2003/013227, WO2003/013228, WO2003/014327, WO2004/031349, WO2004/076638, WO98/09521, and WO99/38977 describing genes, including CBF genes and transcription factors effective in mitigating the negative effects of freezing, high salinity, and drought on plants, as well as conferring other positive effects on plant phenotype; US2004/0148654 and WO01/36596 where abscisic acid is altered in plants resulting in improved plant phenotype such as increased yield and/or increased tolerance to abiotic stress; WO2000/006341, WO04/090143, U.S. application Ser. Nos. 10/817,483 and 09/545,334 where cytokinin expression is modified resulting in plants with increased stress tolerance, such as drought tolerance, and/or increased yield; WO02/02776, WO2003/052063, JP2002281975, U.S. Pat. No. 6,084,153, WO0164898, U.S. Pat. Nos. 6,177,275, and 6,107,547 (enhancement of nitrogen utilization and altered nitrogen responsiveness); US20040128719, US20030166197 and WO2000/32761 (ethylene alteration); US20040098764 and US20040078852 (plant transcription factors or transcriptional regulators of abiotic stress).

Other genes and transcription factors that affect plant growth and agronomic traits such as yield, flowering, plant growth and/or plant structure, can be introduced or introgressed into plants. See, e.g., WO97/49811 (LHY); WO98/56918 (ESD4); WO97/10339 and U.S. Pat. No. 6,573,430 (TFL); U.S. Pat. No. 6,713,663 (FT); WO96/14414 (CON); WO96/38560, WO01/21822 (VRN1); WO00/44918 (VRN2); WO99/49064 (GI); WO00/46358 (FRI); WO97/29123, U.S. Pat. Nos. 6,794,560, 6,307,126 (GAI); WO99/09174 (D8 and Rht); WO2004/076638 and WO2004/031349 (transcription factors). Commercial traits in plants can be created through the expression of genes that alter starch or protein for the production of paper, textiles, ethanol, polymers or other materials with industrial uses.

3. Genes that Control Male-sterility

There are several methods of conferring genetic male sterility available, such as multiple mutant genes at separate locations within the genome that confer male sterility, as disclosed in U.S. Pat. Nos. 4,654,465 and 4,727,219 to Brar et al. and chromosomal translocations as described by Patterson in U.S. Pat. Nos. 3,861,709 and 3,710,511. In addition to these methods, Albertsen et al., U.S. Pat. No. 5,432,068, describe a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

(A) Introduction of a deacetylase gene under the control of a tapetum-specific promoter and with the application of the chemical N-Ac-PPT. See WO 01/29237.

(B) Introduction of various stamen-specific promoters. See WO 92/13956, WO 92/13957.

(C) Introduction of the barnase and the barstar gene. See Paul et al. *Plant Mol. Biol.* 19:611-622, 1992.

For additional examples of nuclear male and female sterility systems and genes, see also U.S. Pat. Nos. 5,859,341; 6,297,426; 5,478,369; 5,824,524; 5,850,014; and 6,265,640.

4. Genes that create a site for site specific DNA integration. This includes the introduction of FRT sites that may be used in the FLP/FRT system and/or Lox sites that may be used in the Cre/Loxp system. See, e.g., Lyznik, et al., Site-Specific Recombination for Genetic Engineering in Plants, *Plant Cell Rep* (2003) 21:925-932; WO 99/25821, which are hereby incorporated by reference. Other systems that may be used include the Gin recombinase of phage Mu (Maeser et al., 1991, *Mol Gen Genet.;*230(1-2):170-6.); Vicki Chandler, *The Maize Handbook* ch. 118 (Springer-Verlag 1994), the Pin recombinase of *E. coli* (Enomoto et al., 1983), and the R/RS system of the pSR1 plasmid (Araki et al., 1992. *J Mol Biol.* 5;225(1):25-37.

Means of increasing or inhibiting a protein are well known to one skilled in the art and, by way of example, may include, transgenic expression, antisense suppression, co-suppression methods including but not limited to: RNA interference, gene activation or suppression using transcription factors and/or repressors, mutagenesis including transposon tagging, directed and site-specific mutagenesis, chromosome engineering (see Nobrega et. al., *Nature* 431:988-993(04)), homologous recombination, TILLING (Targeting Induced Local Lesions In Genomes), and biosynthetic competition to manipulate, the expression of proteins.

Many techniques for gene silencing are well known to one of skill in the art, including but not limited to knock-outs (such as by insertion of a transposable element such as Mu, Vicki Chandler, *The Maize Handbook* ch. 118 (Springer-Verlag 1994) or other genetic elements such as a FRT, Lox or other site specific integration site; RNA interference (Napoli et al. (1990) *Plant Cell* 2:279-289; U.S. Pat. No. 5,034,323, Sharp (1999) *Genes Dev.* 13:139-141, Zamore et al. (2000) *Cell* 101:25-33; and Montgomery et al. (1998) *PNAS USA* 95:15502-15507); virus-induced gene silencing (Burton, et al. (2000) *Plant Cell* 12:691-705, and Baulcombe (1999) *Curr. Op. Plant Bio.* 2:109-113); target-RNA-specific ribozymes (Haseloff et al. (1988) *Nature* 334: 585-591); hairpin structures (Smith et al. (2000) *Nature* 407:319-320; WO 99/53050; and WO 98/53083); MicroRNA (Aukerman & Sakai (2003) *Plant Cell* 15:2730-2741); ribozymes (Steinecke et al. (1992) *EMBO J.* 11:1525, and Perriman et al. (1993) *Antisense Res. Dev.* 3:253); oligonucleotide mediated targeted modification (e.g., WO 03/076574 and WO 99/25853); zinc-finger targeted molecules (e.g., WO 01/52620; WO 03/048345; and WO 00/42219); and other methods or combinations of the above methods known to those of skill in the art.

Any method of increasing or inhibiting a protein can be used in the present invention. Several examples are outlined in more detail below for illustrative purposes.

The nucleotide sequence operably linked to the regulatory elements disclosed herein can be an antisense sequence for a targeted gene. See, e.g., Sheehy et al. (1988) *PNAS USA* 85:8805-8809; U.S. Pat. Nos. 5,107,065; 5,453, 566; 5,759, 829. By "antisense DNA nucleotide sequence" is intended a sequence that is in inverse orientation to the 5'-to-3' normal orientation of that nucleotide sequence. When delivered into a plant cell, expression of the antisense DNA sequence prevents normal expression of the DNA nucleotide sequence for the targeted gene. The antisense nucleotide sequence encodes an RNA transcript that is complementary to and capable of hybridizing with the endogenous messenger RNA (mRNA) produced by transcription of the DNA nucleotide sequence for the targeted gene. In this case, production of the native protein encoded by the targeted gene is inhibited to achieve a desired phenotypic response. Thus the regulatory sequences disclosed herein can be operably linked to antisense DNA sequences to reduce or inhibit expression of a native protein in the plant seed.

As noted, other potential approaches to impact expression of proteins in the seed include traditional co-suppression, that is, inhibition of expression of an endogenous gene through the expression of an identical structural gene or gene fragment introduced through transformation (Goring, D. R., Thomson, L., Rothstein, S. J. 1991. Proc. *Natl. Acad Sci. USA* 88:1770-1774 co-suppression; Taylor (1997) *Plant Cell* 9:1245; Jorgensen (1990) *Trends Biotech.* 8(12):340-344; Flavell (1994) *PNAS* USA 91:3490-3496; Finnegan et al. (1994) *Bio/Technology* 12: 883-888; and Neuhuber et al. (1994) *Mol. Gen. Genet.* 244:230-241). In one example, co-suppression can be achieved by linking the promoter to a DNA segment such that transcripts of the segment are produced in the sense orientation and where the transcripts have at least 65% sequence identity to transcripts of the endogenous gene of interest, thereby suppressing expression of the endogenous gene in said plant cell. See U.S. Pat. No. 5,283, 184. The endogenous gene targeted for co-suppression may be a gene encoding any protein that accumulates in the plant species of interest. For example, where the endogenous gene targeted for co-suppression is the 50 kD gamma-zein gene, co-suppression is achieved using an expression cassette comprising the 50 kD gamma-zein gene sequence, or variant or fragment thereof.

Additional methods of co-suppression are known in the art and can be similarly applied to the instant invention. These methods involve the silencing of a targeted gene by spliced hairpin RNA's and similar methods also called RNA interference and promoter silencing. See Smith et al. (2000) *Nature* 407:319-320; Waterhouse and Helliwell (2003)) *Nat. Rev. Genet.* 4:29-38; Waterhouse et al. (1998) *Proc. Natl. Acad. Sci. USA* 95:13959-13964; Chuang and Meyerowitz (2000) *Proc. Natl. Acad. Sci. USA* 97:4985-4990; Stoutjesdijk et al. (2002) *Plant Phystiol.* 129:1723-1731; Patent Applications WO 99/53050; WO 99/49029; WO 99/61631; WO 00/49035; U.S. Pat. No. 6,506,559.

For mRNA interference, the expression cassette is designed to express an RNA molecule that is modeled on an endogenous miRNA gene. The miRNA gene encodes an RNA that forms a hairpin structure containing a 22-nucleotide sequence that is complementary to another endogenous gene (target sequence). miRNA molecules are highly efficient at inhibiting the expression of endogenous genes, and the RNA interference they induce is inherited by subsequent generations of plants.

In one embodiment, the polynucleotide to be introduced into the plant comprises an inhibitory sequence that encodes a zinc finger protein that binds to a gene encoding a protein of the invention resulting in reduced expression of the gene. In particular embodiments, the zinc finger protein binds to a regulatory region of a gene of the invention. In other embodiments, the zinc finger protein binds to a messenger RNA encoding a protein and prevents its translation. Methods of selecting sites for targeting by zinc finger proteins have been described, for example, in U.S. Pat. No. 6,453,242, and methods for using zinc finger proteins to inhibit the expression of genes in plants are described, for example, in U.S. Patent Publication No. 20030037355.

The expression cassette may also include at the 3' terminus of the isolated nucleotide sequence of interest, a transcriptional and translational termination region functional in plants. The termination region can be native with the promoter nucleotide sequence of the present invention, can be native with the DNA sequence of interest, or can be derived from another source.

Any convenient termination regions can be used in conjunction with the promoter of the invention, and are available from the Ti-plasmid of *A. tumefaciens*, such as the octopine synthase and nopaline synthase termination regions. See Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. 1989) *Nucleic Acids Res.* 17:7891-7903; Joshi et al. (1987) *Nucleic Acid Res.* 15:9627-9639.

The expression cassettes can additionally contain 5' leader sequences. Such leader sequences can act to enhance translation. Translation leaders are known in the art and include: picornavirus leaders, for example, EMCV leader (Encephalomyocarditis 5' noncoding region), Elroy-Stein et al. (1989) *Proc. Natl. Acad. Sci. USA* 86:6126-6130; potyvirus leaders, for example, TEV leader (Tobacco Etch Virus), Allison et al. (1986); MDMV leader (Maize Dwarf Mosaic Virus), *Virology* 154:9-20; human immunoglobulin heavy-chain binding protein (BiP), Macejak et al. (1991) *Nature* 353:90-94; untranslated leader from the coat protein mRNA of alfalfa mosaic virus (AMV RNA 4), Jobling et al. (1987) *Nature*

325:622-625); tobacco mosaic virus leader (TMV), Gallie et al. (1989) *Molecular Biology of RNA*, pages 237-256; and maize chlorotic mottle virus leader (MCMV), Lommel et al. (1991) *Virology* 81:382-385. See also Della-Cioppa et al. (1987) *Plant Physiology* 84:965-968. The cassette can also contain sequences that enhance translation and/or mRNA stability such as introns.

In those instances where it is desirable to have an expressed product of an isolated nucleotide sequence directed to a particular organelle, particularly the plastid, amyloplast, or to the endoplasmic reticulum, or secreted at the cell's surface or extracellularly, the expression cassette can further comprise a coding sequence for a transit peptide. Such transit peptides are well known in the art and include, but are not limited to: the transit peptide for the acyl carrier protein, the small subunit of RUBISCO, plant EPSP synthase, and the like.

In preparing the expression cassette, the various DNA fragments can be manipulated, so as to provide for the DNA sequences in the proper orientation and, as appropriate, in the proper reading frame. Toward this end, adapters or linkers can be employed to join the DNA fragments or other manipulations can be involved to provide for convenient restriction sites, removal of superfluous DNA, removal of restriction sites, or the like. For this purpose, in vitro mutagenesis, primer repair, restriction digests, annealing, and resubstitutions such as transitions and transversions, can be involved.

As noted herein, the present invention provides vectors capable of expressing genes of interest under the control of the regulatory elements. In general, the vectors should be functional in plant cells. At times, it may be preferable to have vectors that are functional in *E. coli* (e.g., production of protein for raising antibodies, DNA sequence analysis, construction of inserts, obtaining quantities of nucleic acids). Vectors and procedures for cloning and expression in *E. coli* are discussed in Sambrook et al. (supra).

The transformation vector comprising the regulatory sequences of the present invention operably linked to an isolated nucleotide sequence in an expression cassette, can also contain at least one additional nucleotide sequence for a gene to be cotransformed into the organism. Alternatively, the additional sequence(s) can be provided on another transformation vector.

Vectors that are functional in plants can be binary plasmids derived from *Agrobacterium*. Such vectors are capable of transforming plant cells. These vectors contain left and right border sequences that are required for integration into the host (plant) chromosome. At minimum, between these border sequences is the gene to be expressed under control of the regulatory elements of the present invention. In one embodiment, a selectable marker and a reporter gene are also included. For ease of obtaining sufficient quantities of vector, a bacterial origin that allows replication in *E. coli* can be used.

Reporter genes can be included in the transformation vectors. Examples of suitable reporter genes known in the art can be found in, for example: Jefferson et al. (1991) in *Plant Molecular Biology Manual*, ed. Gelvin et al. (Kluwer Academic Publishers), pp. 1-33; DeWet et al. (1987) *Mol. Cell. Biol.* 7:725-737; Goff et al. (1990) *EMBO J.* 9:2517-2522; Kain et al. (1995) *BioTechniques* 19:650-655; and Chiu et al. (1996) *Current Biology* 6:325-330.

Selectable marker genes for selection of transformed cells or tissues can be included in the transformation vectors. These can include genes that confer antibiotic resistance or resistance to herbicides. Examples of suitable selectable marker genes include, but are not limited to: genes encoding resistance to chloramphenicol, Herrera Estrella et al. (1983) *EMBO J.* 2:987-992; methotrexate, Herrera Estrella et al. (1983) *Nature* 303:209-213; Meijer et al. (1991) *Plant Mol. Biol.* 16:807-820; hygromycin, Waldron et al. (1985) *Plant Mol. Biol.* 5:103-108; Zhijian et al. (1995) *Plant Science* 108:219-227; streptomycin, Jones et al. (1987) *Mol. Gen. Genet.* 210:86-91; spectinomycin, Bretagne-Sagnard et al. (1996) *Transgenic Res.* 5:131-137; bleomycin, Hille et al. (1990) *Plant Mol. Biol.* 7:171-176; sulfonamide, Guerineau et al. (1990) *Plant Mol. Biol.* 15:127-136; bromoxynil, Stalker et al. (1988) *Science* 242:419-423; glyphosate, Shaw et al. (1986) *Science* 233:478-481; phosphinothricin, DeBlock et al. (1987) *EMBO J.* 6:2513-2518.

Further, when linking a seed promoter of the invention with a nucleotide sequence encoding a detectable protein, expression of a linked sequence can be tracked in the seed, thereby providing a useful so-called screenable or scorable markers. The expression of the linked protein can be detected without the necessity of destroying tissue. More recently, interest has increased in utilization of screenable or scorable markers. By way of example without limitation, the promoter can be linked with detectable markers including a β-glucuronidase, or uidA gene (GUS), which encodes an enzyme for which various chromogenic substrates are known (Jefferson, R. A. et al., 1986, *Proc. Natl. Acad. Sci. USA* 83:8447-8451); maize-optimized phosphinothricin acetyl transferase (moPAT); chloramphenicol acetyl transferase; alkaline phosphatase; a R-locus gene, which encodes a product that regulates the production of anthocyanin pigments (red color) in plant tissues (Dellaporta et al., in *Chromosome Structure and Function*, Kluwer Academic Publishers, Appels and Gustafson eds., pp. 263-282 (1988); Ludwig et al. (1990) *Science* 247:449); a p-lactamase gene (Sutcliffe, *Proc. Nat'l. Acad. Sci. U.S.A.* 75:3737 (1978)), which encodes an enzyme for which various chromogenic substrates are known (e.g., PADAC, a chromogenic cephalosporin); a xylE gene (Zukowsky et al., *Proc. Nat'l. Acad. Sci. U.S.A.* 80:1101 (1983)), which encodes a catechol dioxygenase that can convert chromogenic catechols; an α-amylase gene (Ikuta et al., *Biotech.* 8:241 (1990)); a tyrosinase gene (Katz et al., *J. Gen. Microbiol.* 129:2703 (1983)), which encodes an enzyme capable of oxidizing tyrosine to DOPA and dopaquinone, which in turn condenses to form the easily detectable compound melanin a green fluorescent protein (GFP) gene (Sheen et al., *Plant J.* 8(5):777-84 (1995)) ; a lux gene, which encodes a luciferase, the presence of which may be detected using, for example, X-ray film, scintillation counting, fluorescent spectrophotometry, low-light video cameras, photon counting cameras or multiwell luminometry (Teeri et al. (1989) *EMBO J.* 8:343); DS-RED EXPRESS (Matz, M. V. et al. (1999) *Nature Biotech.* 17:969-973, Bevis B. J. et al. (2002) *Nature Biotech* 20:83-87, Haas, J. et al. (1996) *Curr. Biol.* 6:315-324); *Zoanthus* sp. yellow fluorescent protein (ZsYellow) that has been engineered for brighter fluorescence (Matz et al. (1999) *Nature Biotech.* 17:969-973, available from BD Biosciences Clontech, Palo Alto, Calif., USA, catalog no. K6100-1); and cyan florescent protein (CYP) (Bolte et al. (2004) *J. Cell Science* 117:943-54 and Kato et al. (2002) *Plant Physiol* 129:913-42).

The methods of the invention involve introducing a polypeptide or polynucleotide into a plant. "Introducing" is intended to mean presenting to the plant the polynucleotide or polypeptide in such a manner that the sequence gains access to the interior of a cell of the plant. The methods of the invention do not depend on a particular method for introducing a sequence into a plant, only that the polynucleotide or polypeptides gains access to the interior of at least one cell of the plant. Methods for introducing polynucleotide or polypeptides into plants are known in the art including, but not limited to, stable transformation methods and transient transformation methods.

"Stable transformation" is intended to mean that the nucleotide construct introduced into a plant integrates into the genome of the plant and is capable of being inherited by the progeny thereof. "Transient transformation" is intended to mean that a polynucleotide is introduced into the plant and does not integrate into the genome of the plant or a polypeptide is introduced into a plant.

A transformation vector comprising the particular regulatory sequences of the present invention, operably linked to an isolated nucleotide sequence of interest in an expression cassette, can be used to transform any plant. In this manner, genetically modified plants, plant cells, plant tissue, seed, and the like can be obtained. Transformation protocols can vary depending on the type of plant or plant cell, i.e., monocot or dicot, targeted for transformation. Suitable methods of transforming plant cells include microinjection, Crossway et al. (1986) *Biotechniques* 4:320-334; electroporation, Riggs et al. (1986) *Proc. Natl. Acad. Sci. USA* 83:5602-5606; *Agrobacterium*-mediated transformation, see for example, Townsend et al. U.S. Pat. No. 5,563,055; direct gene transfer, Paszkowski et al. (1984) *EMBO J.* 3:2717-2722; and ballistic particle acceleration, see for example, Sanford et al. U.S. Pat. No. 4,945,050, Tomes et al. (1995) in *Plant Cell, Tissue, and Organ Culture: Fundamental Methods*, ed. Gamborg and Phillips (Springer-Verlag, Berlin); and McCabe et al. (1988) *Biotechnology* 6:923-926; see also Weissinger et al. (1988) Annual Rev. Genet. 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Datta et al. (1990) *Bio/Technology* 8:736-740 (rice); Klein et al. (1988) *Proc. Natl. Acad. Sci. USA* 85:4305-4309 (maize); Klein et al. (1988) *Biotechnology* 6:559-563 (maize); Klein et al. (1988) *Plant Physiol.* 91:440-444 (maize); Fromm et al. (1990) *Biotechnology* 8:833-839; Hooydaas-Van Slogteren et al. (1984) Nature (London) 311:763-764; Bytebier et al. (1987) *Proc. Natl. Acad. Sci. USA* 84:5345-5349 (Liliaceae); De Wet et al. (1985) in *The Experimental Manipulation of Ovule Tissues*, ed. G. P. Chapman et al. (Longman, New York), pp. 197-209 (pollen); Kaeppler et al. (1990) *Plant Cell Reports* 9:415-418; and Kaeppler et al. (1992) *Theor. Appl. Genet.* 84:560-566 (whisker-mediated transformation); D. Halluin et al. (1992) *Plant Cell* 4:1495-1505 (electroporation); Li et al. (1993) *Plant Cell Reports* 12:250-255 and Christou et al. (1995) *Annals of Botany* 75:407-413 (rice); Osjoda et al. (1996) *Nature Biotechnology* 14:745-750 (maize via *Agrobacterium tumefaciens*).

In specific embodiments, a polynucleotides comprising a promoter of the invention can be provided to a plant using a variety of transient transformation methods. The polynucleotide can be transiently transformed into the plant using techniques known in the art. Such techniques include viral vector system and the precipitation of the polynucleotide in a manner that precludes subsequent release of the DNA. Thus, the transcription from the particle-bound DNA can occur, but the frequency with which its released to become integrated into the genome is greatly reduced. Such methods include the use particles coated with polyethylimine (PEI; Sigma #P3143). See, for example, Crossway et al. (1986) *Mol Gen. Genet.* 202:179-185; Nomura et al. (1986) *Plant Sci.* 44:53-58; Hepler et al. (1994) *Proc. Natl. Acad. Sci.* 91: 2176-2180 and Hush et al. (1994) *The Journal of Cell Science* 107:775-784, all of which are herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference.

Briefly, the polynucleotide of the invention can be contained in transfer cassette flanked by two non-recombinogenic recombination sites. The transfer cassette is introduced into a plant having stably incorporated into its genome a target site which is flanked by two non-recombinogenic recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed can be grown into plants in accordance with conventional methods. See, for example, McCormick et al. (1986) *Plant Cell Reports* 5:81-84. These plants can then be grown and pollinated with the same transformed strain or different strains. The resulting plant having seed-preferred expression of the desired phenotypic characteristic can then be identified. Two or more generations can be grown to ensure that seed-preferred expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a polynucleotide of the invention, for example, an expression cassette of the invention, stably incorporated into their genome.

As used herein, the term plant also includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

The present invention may be used for transformation of any plant species, including, but not limited to, monocots and dicots. Examples of plant species of interest include, but are not limited to, corn (*Zea mays*), Brassica sp. (e.g., *B. napus, B. rapa, B. juncea*), particularly those Brassica species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Peryea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia*

*integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). In specific embodiments, plants of the present invention are crop plants (for example, corn, alfalfa, sunflower, *Brassica*, soybean, cotton, safflower, peanut, sorghum, wheat, millet, tobacco, etc.). In other embodiments, corn and soybean and sugarcane plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

The following examples are offered by way of illustration and not by way of limitation.

EXAMPLES

Regulatory regions from maize 17 KD OLE were isolated from maize plants and cloned. maize 17 KD OLE was selected as a source of seed-preferred regulatory elements based on the spatial and temporal expression of its products.

Example 1

Prediction of Expression Via Lynx MPSS

Lynx™ gene expression profiling technology was used to identify the maize 17 KD OLE coding region as a candidate for promoter isolation. Massively parallel signature sequencing (MPSS, see Brenner et al, *Nature Biotechnology* 18:630-634, 2000) indicated expression in various tissues at about 18 DAP (days after pollination) in seed, peaking at about 50 k ppm. Results are summarized in FIG. 2A. MPSS data showed no significant expression of maize 17 KD OLE (17 kilodalton oleosin) in flowering or vegetative tissue.

Example 2

Expression Data Using Promoter Sequences

A promoter::ZS-YELLOW::terminator fusion construct was prepared as set out below. ZS-YELLOW is a scorable marker (Matz, M. V. et al 91999) *Nature Biotech.* 17:969-973, Bevis B. J. et al. (2002) *Nature Biotech* 20:83-87, Haas, J. et al. (1996) *Curr. Biol.* 6:315-324). All vectors were constructed using standard molecular biology techniques (Sambrook et al., supra). The fusion construct is constructed as follows: maize 17 KD OLE PRO (SEQ ID NO: 1): ZS-YELLOW:PINII TERM.

Successful subcloning was confirmed by restriction analysis. Transformation and expression was confirmed as discussed infra.

Example 3

Confirmation of Expression

The construct described above was inserted into the genome of various *zea mays* plants through techniques well-known in the art. Seed was collected at 14, 16, 22, and 27 days after pollination. The collected seed was bisected and examined under a microscope with the appropriate filter to detect the expression of the ZS-YELLOW marker. Photographs were taken of seeds at 4, 16, 22, and 27 days after pollination. The photographs are shown herewith as FIGS. 3*a*-*d*. As can be seen the results demonstrate preferred expression of the ZS-YELLOW marker in the embryo and aleurone.

Example 4

Expression Using Truncated Promoter Sequence

In addition to the testing of the full maize 17 KD OLE promoter described in Examples 1-3 above, similar tests may be conducted on a truncation of the maize 17 KD OLE promoter, designated the maize 17 KD OLE B sequence. Similar to the procedure described in Example 2, a fusion construct may be produced as follows: maize 17 KD OLEB PRO:DS-ZS-YELLOW:PINII TERM. Photographs are taken of seeds at various says after pollination, and if a functional truncation, will show preferred expression of the DS-ZS-YELLOW marker in the embryo and aleurone, similar to the results seen with the full maize 17 KD OLE promoter described in Example 3 supra.

The article "a" and "an" are used herein to refer to one or more than one (i.e., to at least one) of the grammatical object of the article. By way of example, "an element" means one or more element.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

We claim:

1. An isolated promoter comprising the nucleotide sequence of SEQ ID NO:1.

2. A recombinant expression cassette comprising a promoter operably linked to a nucleic acid of interest, wherein the promoter comprises the nucleotide sequence of SEQ ID NO:1.

3. A vector comprising a recombinant expression cassette comprising a promoter operably linked to a nucleic acid of interest, wherein the promoter comprises the nucleotide sequence of SEQ ID NO:1.

4. A plant cell stably transformed with a polynucleotide molecule comprising a promoter, wherein the promoter comprises the nucleotide sequence of SEQ ID NO:1.

5. The plant cell of claim 4, wherein the polynucleotide molecule further comprises a nucleic acid of interest operably linked for expression to the promoter.

6. The plant cell of claim 4, wherein the plant cell is a monocot or dicot plant cell.

7. The plant cell of claim 4, wherein the plant cell is a maize, wheat, rice, millet, barley, sorghum, rye, soybean, alfalfa, oilseed Brassica, cotton, sunflower, potato, or tomato plant cell.

8. The plant cell of claim 4, wherein the plant cell is a seed cell.

9. A plant stably transformed with a polynucleotide molecule comprising the nucleotide sequence of SEQ ID NO:1.

10. The plant of claim 9, wherein said polynucleotide molecule further comprises a nucleic acid of interest operably linked for expression to the nucleotide sequence.

11. The plant of claim 9, wherein the plant is a monocot or dicot.

12. The plant of claim 9, wherein the plant is maize, wheat, rice, millet, barley, sorghum, rye, soybean, alfalfa, oilseed Brassica, cotton, sunflower, potato, or tomato.

13. The plant of claim 9, wherein the plant is maize.

14. The plant of claim 9, wherein the plant is a seed.

15. A method for modulating expression of a nucleic acid of interest in a plant, said method comprising:
 (a) introducing into a plant cell or tissue a polynucleotide molecule comprising a promoter operably linked to the nucleic acid of interest, wherein the promoter comprises the nucleotide sequence of SEQ ID NO:1; and
 (b) regenerating a plant from the plant cell wherein expression of the nucleic acid of interest is modulated compared to the wild-type.

16. The method of claim 15, wherein the nucleic acid of interest is selected from the group consisting of nucleic acids providing improved output traits, nucleic acids providing improved agronomic traits, nucleic acids providing resistance to insects, nucleic acids providing resistance to disease and nucleic acids providing herbicide resistance.

17. The method of claim 15, wherein the nucleic acid of interest is a nucleic acid providing improved output traits.

18. The method of claim 15, wherein the plant is a monocot or dicot.

19. The method of claim 15, wherein the plant is maize, wheat, rice, millet, barley, sorghum, rye, soybean, alfalfa, oilseed *Brassica*, cotton, sunflower, potato, or tomato.

* * * * *